United States Patent
Pattison et al.

(10) Patent No.: US 9,792,411 B2
(45) Date of Patent: Oct. 17, 2017

(54) POROELASTIC DYNAMIC MECHANICAL ANALYZER FOR DETERMINING MECHANICAL PROPERTIES OF BIOLOGICAL MATERIALS

(71) Applicant: The Trustees of Dartmouth College, Hanover, NH (US)

(72) Inventors: Adam J. Pattison, West Lebanon, NH (US); Matthew D J McGarry, Etna, NH (US); Keith D. Paulsen, Hanover, NH (US); John B. Weaver, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 1221 days.

(21) Appl. No.: 13/831,160

(22) Filed: Mar. 14, 2013

(65) Prior Publication Data
US 2014/0276230 A1 Sep. 18, 2014

(51) Int. Cl.
*A61B 5/103* (2006.01)
*A61B 5/117* (2016.01)
(Continued)

(52) U.S. Cl.
CPC ........ *G06F 19/3437* (2013.01); *A61B 5/0051* (2013.01); *A61B 5/055* (2013.01);
(Continued)

(58) Field of Classification Search
CPC ... E21B 43/26; E21B 49/006; A61K 2300/00; A61K 31/727; A61K 31/728;
(Continued)

(56) References Cited

U.S. PATENT DOCUMENTS 5,474,070 A * 12/1995 Ophir .................. A61B 5/0048
600/437
6,066,095 A * 5/2000 Morsy .................. G06T 7/2033
600/438
(Continued)

OTHER PUBLICATIONS

Perrinez, Phillip R., "Modeling of Soft Poroelastic Tissue in Time-Harmonic MR Elastography," IEEE Transactions on Biomedical Engineering, vol. 56, No. 3, Mar. 2009, pp. 598-608.
(Continued)

*Primary Examiner* — Rene Towa
*Assistant Examiner* — May Abouelela
(74) *Attorney, Agent, or Firm* — Lathrop Gage LLP (57) ABSTRACT

A system for determining parameters of porous media or material, which in an embodiment is biological tissue, includes an actuator and a displacement monitor. The actuator is adapted to apply a displacement to tissue at a particular frequency selected from a range of frequencies, and the force monitor adapted to monitor a mechanical response of tissue. The system also has a processor coupled to drive the actuator and to read the mechanical response, the processor coupled to execute from memory a poroelastic model of mechanical properties of the material, and a convergence procedure for determining parameters for the poroelastic model such that the model predicts mechanical response of the tissue to within limits.

13 Claims, 4 Drawing Sheets (51) Int. Cl.
*G06F 19/00* (2011.01)
*G01N 3/32* (2006.01)
*A61B 5/00* (2006.01)
*A61B 5/055* (2006.01)
*G01R 33/563* (2006.01)
*A61B 5/11* (2006.01)

(52) U.S. Cl.
CPC .......... *A61B 5/4064* (2013.01); *A61B 5/6868* (2013.01); *G01N 3/32* (2013.01); *G06F 19/3481* (2013.01); *A61B 5/1128* (2013.01); *G01N 2203/0005* (2013.01); *G01N 2203/0069* (2013.01); *G01N 2203/0073* (2013.01); *G01N 2203/0094* (2013.01); *G01N 2203/0218* (2013.01); *G01R 33/56358* (2013.01)

(58) Field of Classification Search
CPC ...... A61K 31/737; A61K 35/15; A61K 35/16; A61K 35/18; A61K 35/19; A61K 38/363; A61K 38/4833; A61K 38/4846; A61K 35/32
USPC ....................................... 600/587; 73/862.637
See application file for complete search history.

(56) References Cited

U.S. PATENT DOCUMENTS

| | | | |
|---|---|---|---|
| 6,270,459 B1 * | 8/2001 | Konofagou | A61B 5/0053 600/449 |
| 6,289,753 B1 * | 9/2001 | Basser | G01N 33/4833 73/866 |
| 6,352,507 B1 * | 3/2002 | Torp | A61B 8/485 600/438 |
| 7,553,283 B2 * | 6/2009 | Sandrin | A61B 8/0825 600/438 |
| 7,779,692 B2 * | 8/2010 | Righetti | A61B 5/442 73/602 |
| 7,922,674 B2 * | 4/2011 | Sarvazyan | A61B 5/1077 600/587 |
| 7,935,058 B2 * | 5/2011 | Dupps, Jr. | A61B 3/10 600/398 |
| 8,098,921 B2 * | 1/2012 | Matsumura | A61B 8/08 382/133 |
| 8,187,185 B2 * | 5/2012 | Sakai | A61B 8/0875 600/437 |
| 8,429,982 B2 * | 4/2013 | Sumi | A61B 8/08 73/789 |
| 8,784,317 B2 * | 7/2014 | Taki | A61B 8/0833 382/128 |
| 2009/0275837 A1 * | 11/2009 | Shiina | A61B 8/08 600/459 |
| 2011/0083511 A1 * | 4/2011 | Taki | A61B 8/0833 73/602 |

OTHER PUBLICATIONS

Perrinez, Phillip R., "Magnetic Resonance Poroelastography: an Algorithm for Estimating the Mechanical Properties of Fluid-Saturated Soft Tissues," IEEE Transactions on Medical Imaging, vol. 29, No. 3, Mar. 2010, pp. 746-755.

Perrinez, Phillip R., "Contrast Detection in Fluid-Saturated Media With Magnetic Resonance Poroelastography," Med. Phys. 37(7), Jul. 2010, pp. 3518-3526.

* cited by examiner

POROELASTIC DYNAMIC MECHANICAL ANALYZER FOR DETERMINING MECHANICAL PROPERTIES OF BIOLOGICAL MATERIALS

FIELD

The present document relates to the determination of poroelastic parameters for computer models of mechanical properties of materials, and to the field of mechanical modeling of biological materials, including human and animal tissues.

ATTACHMENTS

A copy of *Magnetic Resonance Poroelastography: An Algorithm for Estimating the Mechanical Properties of Fluid-Saturated Soft Tissues*, IEEE Transactions on Medical Imaging, Vol. 29, No. 3, March 2010 is attached as appendix A. This article describes a poroelastic computer model of tissue together with a system for determining parameters for the model.

BACKGROUND

Computer modeling of mechanical properties of biological materials can be of importance in simulating displacement of tissues during surgery, simulating mechanisms of injury and protective devices, and detection of diseased tissues. Tumors, for example, often have different mechanical properties than normal tissues. Many applications of such modeling, including estimating displacement of brain after skull opening during surgery, require an accurate material model with accurate parameters.

Several material models have been used to estimate tissue properties, mainly viscoelasticity. More recently, poroelasticity-based models have been used. While viscoelasticity characterizes tissue as an array of springs and dashpots, poroelasticity models material based on its structural components, specifically as a porous elastic matrix, with the pores saturated with a viscous fluid. This model applies to tissue like brain parenchyma, where the saturating fluid corresponds to approximately 75% of the tissue volume, and other porous tissues that may have different fluid concentrations. The elastic matrix corresponds to structural proteins such as collagen, and the fluid corresponds to cytoplasm, intracellular fluid, and blood. Poroelastic theory accounts for the fact that some of the fluid can be squeezed out of tissue when a pressure gradient is applied, and that fluid flow can damp oscillations in a manner similar to that of a hydraulic shock-absorber. Key to such models is determination of the material parameters (such as shear modulus) to accurately represent tissue.

A prior poroelastic computer algorithm for modeling mechanical properties of tissue and methods of extracting parameters, has been described by Phillip R. Perriñez, Francis E. Kennedy, Elijah E. W. Van Houten, John B. Weaver, and Keith D. Paulsen in *Modeling of Soft Poroelastic Tissue in Time-Harmonic MR Elastography*, IEEE Transactions On Biomedical Engineering, Vol. 56, No. 3, March 2009; and by Phillip R. Perriñez, Francis E. Kennedy, Elijah E. W. Van Houten, John B. Weaver, and Keith D. Paulsen in *Magnetic Resonance Poroelastography: An Algorithm for Estimating the Mechanical Properties of Fluid-Saturated Soft Tissues*, IEEE Transactions On Medical Imaging, Vol. 29, No. 3, March 2010. These publications show the basis of a poroelastic model and illustrate model-data mismatch when using viscoelastic models on poroelastic materials. Furthermore, the work shows that a poroelastic model provides improved numerical and spatial results over prior work using linear elastic and viscoelastic models. The system described in the attached articles requires an expensive magnetic resonance imaging system to measure motion and estimate the model parameters using magnetic resonance elastography (MRE). MRE results for mechanical properties shown in literature for a single tissue range over orders of magnitude. While some variation is expected since tissue is frequency dependent, different model-based reconstructions provide varying estimates due to differing assumptions or model-data mismatch. Therefore, it is important to validate these results with an independent mechanical test, like dynamic mechanical analyzers (DMAs).

Typical DMAs determine viscoelastic model parameters, specifically storage and loss modulus. DMA results are based on the relationship between stress ($\sigma$) and strain ($\epsilon$), which are defined as $\sigma = \sigma_0 \sin(\omega t + \delta)$ and $\epsilon = \epsilon_0 \sin(\omega t + \delta)$, respectively, where $\omega$ is frequency, $\delta$ is the phase lag between the two waves, and $\sigma_0$ and $\epsilon_0$ represent the maximum stress and strain. The storage (stored energy) and loss modulus (dissipated energy) can then be estimated as $E' = \sigma_0/\epsilon_0 (\cos \delta)$ and $E'' = \sigma_0/\epsilon_0 (\sin \delta)$, respectively. A damping ratio is given as $\tan(\delta) = E''/E'$. In viscoelastic theory, the damping forces are modeled by dashpots, where the force is proportional to the velocity, illustrating the frequency dependence of the damping properties. Conversely, in poroelastic theory it is known that due to the biphasic environment, the interaction between the solid and fluid phases causes much of the attenuation. Standard DMAs use different clamps (i.e. compression, 3-point bending) to test different materials. The compression clamp typically has smooth platens that allow the material to slip transversely. Currently, empirical correction factors are used to attempt to correct errors due to this slippage.

SUMMARY

In an embodiment, a system for determining parameters for computer modeling of mechanical responses of material includes an actuator and a force monitor, the actuator adapted to apply a displacement to material at a particular frequency selected from a plurality of frequencies, and the force monitor adapted to monitor a mechanical response of material. The system also has a processor coupled to drive the actuator and to read the mechanical response, the processor coupled to execute a poroelastic model of mechanical properties of material recorded in a memory, and a convergence procedure for determining parameters for the poroelastic model such that the model predicts mechanical response of the material to within limits.

In another embodiment, a method for determining parameters of a computerized mechanical model of a material includes applying a stress to the material with an actuator at a particular frequency selected from a plurality of frequencies, determining a mechanical response to the applied stress; executing machine readable instructions of a poroelastic model of mechanical properties of the material recorded in a memory, the memory also containing limits; and converging parameters for the poroelastic model such that the model predicts mechanical response of the material to within the limits.

DETAILED DESCRIPTION OF THE EMBODIMENTS

A system 100 (FIG. 1) for computer modeling of mechanical properties of material has a dynamic mechanical analyzer (DMA) subsystem 102. The system 100 is particularly suited for modeling of material 110 where the material 110 includes as part or all of the material a porous media saturated with fluid, this class of material includes many types of biological tissues including brain, liver, breast, and many other soft tissues, whether human or animal in origin, DMA subsystem 102 has a frame 104 that provides mechanical support for an actuator 106 that is coupled in series combination with a load cell 108 to apply a mechanical displacement through a platen 109 to a sample of material 110. Platen 109 has a rough, non-slip surface 109A in contact with the material 110. The load cell 108 is arranged to measure forces applied to material 110, and a mechanical displacement-monitoring device 112 is coupled to measure displacements of material 110 induced by the actuator/load-cell combination. The material is placed on a lower platen 113 on stage 114 attached to frame 104. Lower platen 113 also has a rough, non-slip, surface 113A in contact with 110.

Figure 1:
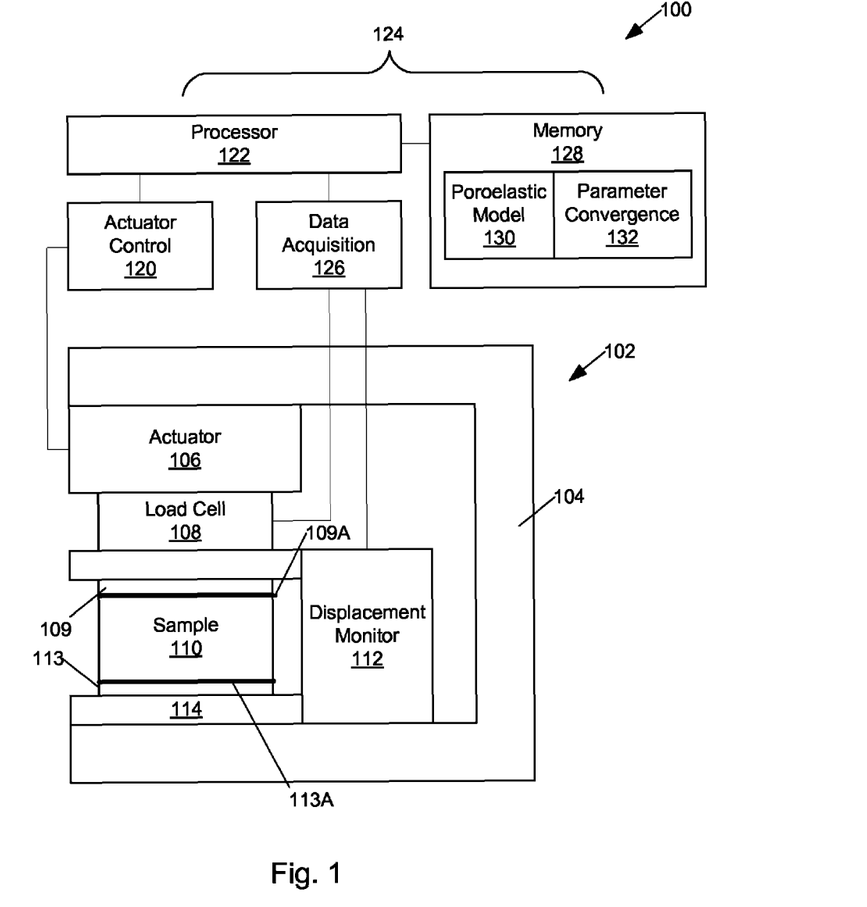
FIG. 1 is a block diagram of a system for determining parameters of a poroelastic material computer model of mechanical properties of biological material, and for executing the poroelastic computer model.

The actuator 106 is driven by an actuator control 120, actuator control 120 is controlled by a processor 122 of a modeling and parameter extraction computer 124, while signals from the load cell 108 and displacement monitor 112 are received through data acquisition circuits 126 into processor 122. Processor 122 is coupled to a memory 128 of computer 124, the memory has computer readable code of the poroelastic computer-executable model 130 and of a convergence routine 132 that permits extraction of model parameters for use in model 130.

Figure 2:
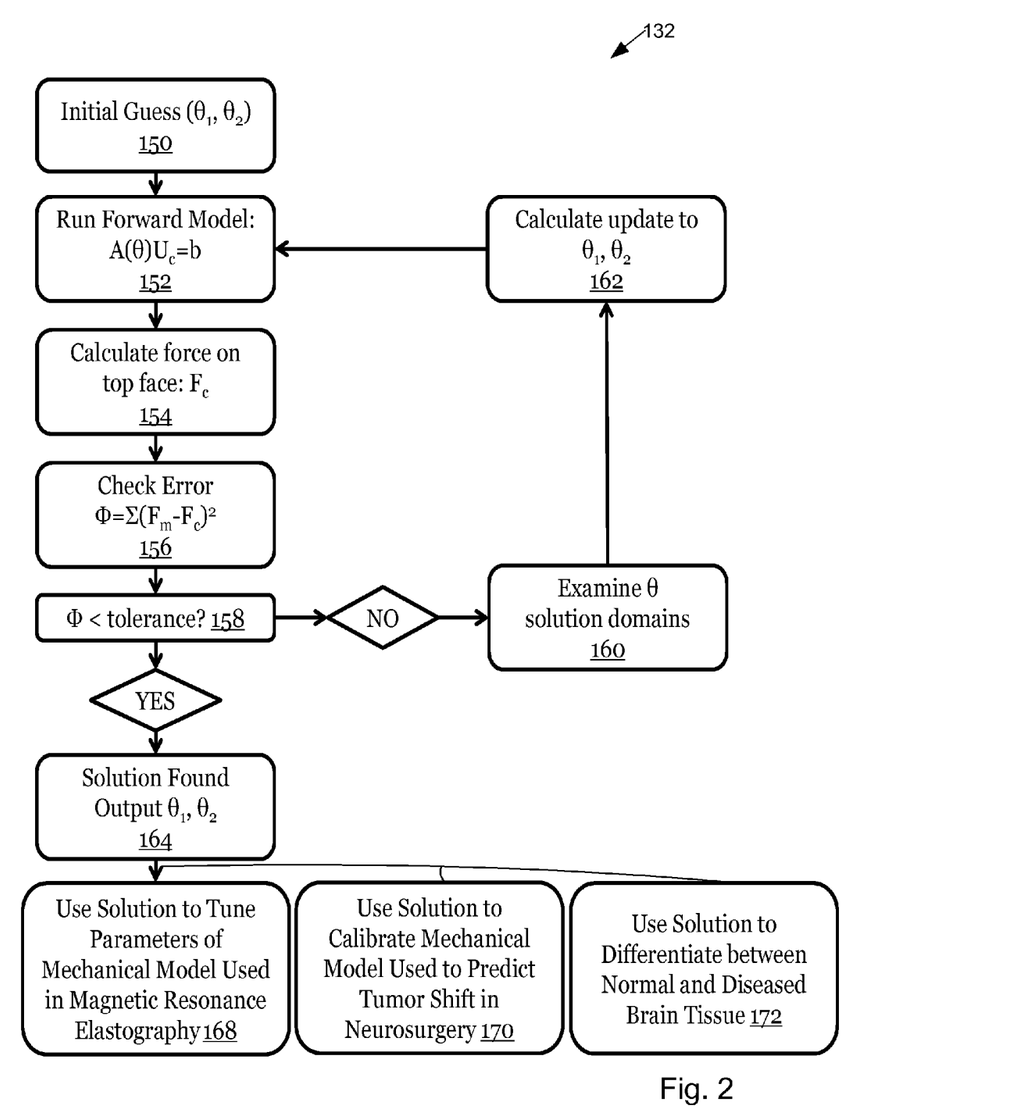
FIG. 2 is a block diagram illustrating a convergence process used to determine parameters of the poroelastic computer model.
Figure 3:
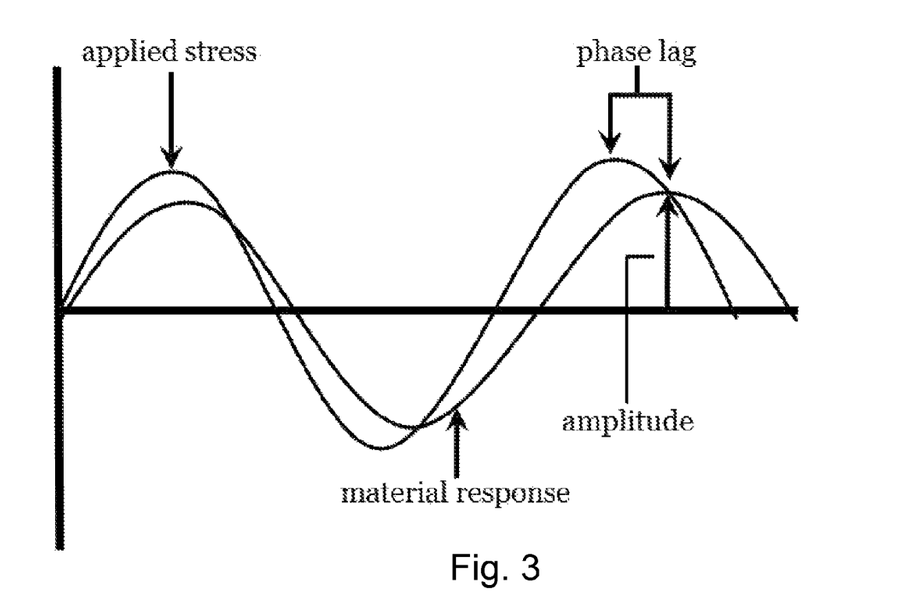
FIG. 3 is an illustration of the typical response of a material to an applied sinusoidal stress in a DMA experiment.

Determination of the model parameters for model 130 is accomplished through a convergence routine 132, as illustrated in FIG. 2. An initial guess 150 of estimated parameters is made, which in an embodiment is determined from a table of parameters associated with known tissue types. The model is executed 152 on the processor 122 using the estimated parameters, which produces a predicted displacement on displacement monitor 112 and then force 154 is estimated on load cell 108. The model results are compared 156 with actual measurements from load cell 108 to determine a difference. In determining the parameters, the actuator 106 is driven in an oscillatory manner to a predetermined displacement at each of several predetermined frequencies to provide stimulus forces that are measured by load cell 108. The amplitude and phase lag of the force of the tissue on the top platen is measured as a material response (FIG. 3) by stimulus monitor 112 at each of the several predetermined frequencies. The frequency-dependent phase lag and amplitude of material response are compared 156 to simulated phase lag and amplitude from the model to determine the model parameters. The difference is then compared 158 to limits, and updated estimated parameters are determined 160, 162. When the model-estimated force results match closely to the actual acquired forces from actuator 106 to within tolerance, the estimated material parameters are output 164.

In a particular embodiment the determined parameters are provided 170 to a computerized model of brain displacement during neurosurgery that embodies a poroelastic model of material properties of brain tissue. When a surgeon opens the skull in a tumor-resection surgery, this model of tumor displacement is performed to determine brain shift to assist the surgeon in removing the tumor.

In an embodiment, the DMA-determined parameters for a particular tissue type are used to validate parameters determined by the MRE system 168. An actuator stimulates the tissue and the mechanical response of the in-vivo tissue is measured by a magnetic resonance imaging system. Poroelastic model parameters, including hydraulic conductivity and shear modulus, are optimized to fit the overall system response to the measured mechanical response, and provide elastograms. Each elastogram presents one model parameter to a surgeon or physician. Since tumorous, Alzheimer's disease-damaged, hydrocephalic, and other abnormal tissue often has mechanical properties differing from normal brain parenchyma, these elastograms may provide information, such as a tumor outline, useful in diagnosis and/or treatment of the subject.

In another embodiment, these parameters are used to detect differences between ex-vivo samples of normal and diseased brain tissue 172. Comparisons of shear modulus and hydraulic conductivity parameter values of normal brain with diseased brain tissue would illustrate how the disease affects the mechanical function of the tissue.

The DMA can be programmed to provide a predetermined displacement, and that displacement is prescribed as a boundary condition in the reconstruction algorithm. In a particular embodiment, the DMA is programmed to provide predetermined displacement through actuator 106 with feedback from displacement monitor 112, while both amplitude and phase of applied force is measured using load cell 108. In an alternative embodiment, the DMA provides a predetermined force from actuator 106 with the actuator force controlled through feedback from load cell 108 while both the displacement amplitude and phase is measured through displacement monitor 112. In both embodiments, the system determines at least a shear modulus and a hydraulic conductivity parameter for the poroelastic computer model.

It has been found difficult to accurately determine dynamic hydraulic conductivity of materials, if the material is allowed to slip along the platens 109, 113. Here, the platens have rough, non-slip, surfaces to prevent transverse boundary displacement along the platens, and the platen contact area is given as a boundary condition in the reconstruction algorithm.

In prior DMA setup, the Poisson's ratio has to be assumed. If the assumption is wrong, the final estimated parameters will be wrong. A second actuation direction allows for more measured independent data without requiring removal and reorienting the material. Combining compression and shearing actuation allows for multiple phase and amplitudes, and, therefore, more model parameters are reconstructed.

Figure 4:
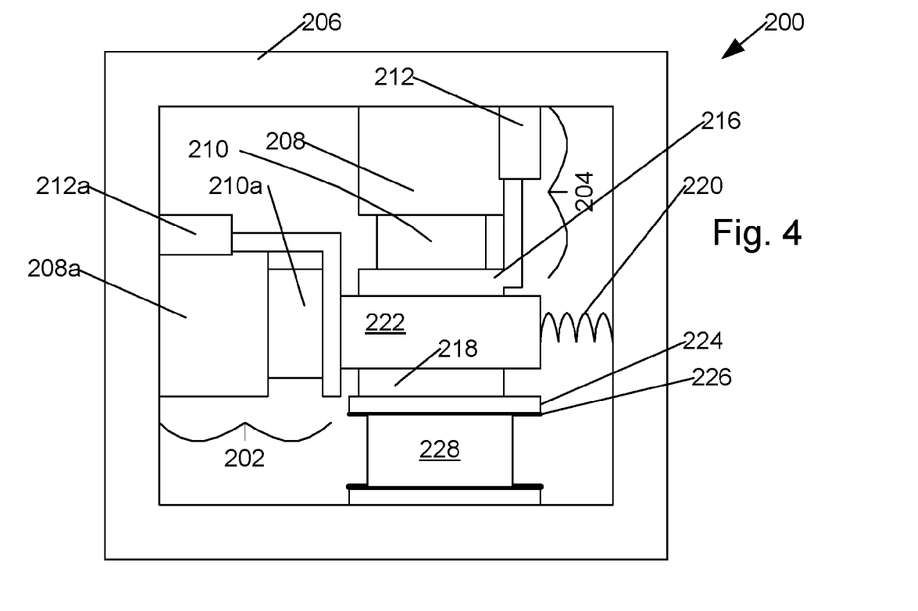
FIG. 4 is an illustration of a two-axis measurement head of a dynamic mechanical analyzer.

The dual-axis DMA head 200, or a similar three-axis head (not illustrated) of FIG. 4 may be used with the modeling and parameter extraction computer 124 of the system of FIG. 1 in place of the single-dimensional DMA head 102 illustrated in FIG. 1. In the dual-axis DMA head, there are two or more actuator-measurement assemblies 202, 204, attached to a frame 206. Each actuator-measurement assembly includes an actuator 208, 208a, a load-cell 210, 210a for measuring pressure, and a displacement monitor 212, 212a. In a particular embodiment, a vertical actuator-measurement assembly 204 applies a Z-axis vibratory motion through a lubricated plate 216 to a puck 218. Puck 218 is enclosed in a frame 222 that applies an X-axis vibratory motion to the puck, such that the puck may be displaced by actuators 208 in both X and Z axes. In some embodiments where actuator 208, 208a is unidirectional, a return spring 220 may be provided to act in concert with actuator 208, 208a; similarly a return spring (not shown) in some embodiments may be associated with the vertical actuator-measurement assembly 204. Platen 224 is attached to puck 218, and has a non-skid surface 226 adapted for applying both X and Z-axis movements to material or tissue 228. Puck 218 is a rectangular lightweight insert that fits in the frame, and is free to slide vertically in the frame. The X-axis actuator moves the frame, and hence the puck, attached platen, and a top surface of the material laterally. The Z-axis actuator applies pressure through lubricated plate 216 to displace the puck vertically within the frame; these vertical displacements are applied through the puck and platen to the material.

In an alternative embodiment, a three-axis DMA head similar to the two-axis head of FIG. 4 has an additional Y-axis actuator assembly also coupled to vibrate the puck.

Figure 5:
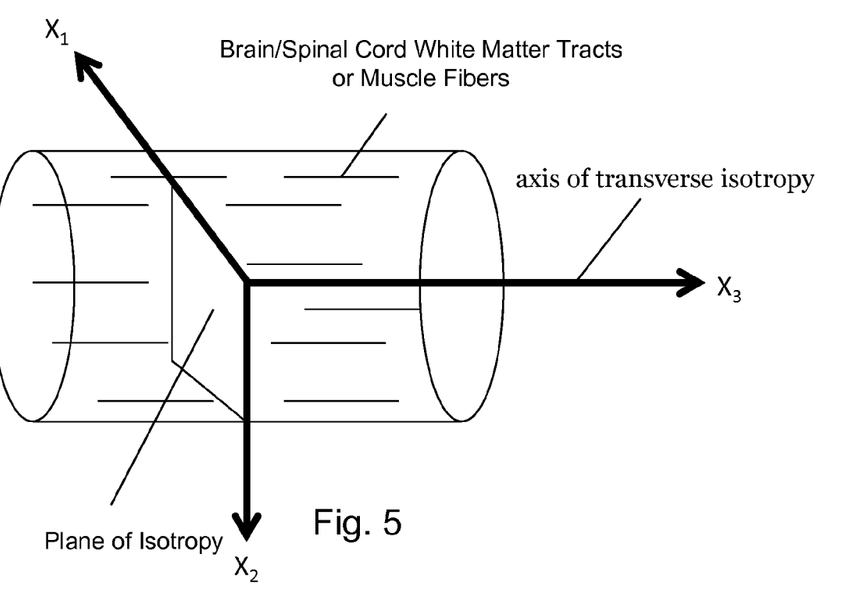
FIG. 5 illustrates multiple axes of anisotropic, or transversely isotropic, poroelastic material such as white matter in brain tissue.

Dual and three-axis DMA head systems, including the dual-axis DMA head of FIG. 4, are particularly suitable for use with tissues such as the white matter of brain and central nervous system, or muscle, because they have anisotropic properties as illustrated in FIG. 5, and thus anisotropic model parameters. These differences in properties with axis are due to the directional fibrous nature of nerve tracts (white matter) or other directionally-oriented fibrous tissue components (muscle, kidney, etc.)

The poroelastic forward model 130 is based on Biot's theory of consolidation, implementing the equations (1a) and (1b):

$$\nabla \cdot \mu(\nabla \bar{u} + \nabla \bar{u}^T) + \nabla(\lambda \nabla \cdot \bar{u}) - (1-\beta)\nabla \bar{p} = -\omega^2(\rho - \beta\rho_f)\bar{u} \quad (1a.)$$

$$i\omega(\nabla \cdot \bar{u}) - \nabla \cdot \bar{q} = 0 \quad (1b.)$$

where $\beta = \dfrac{\omega\phi^2\rho_f\kappa}{i\phi^2 + \kappa\omega(\rho_a + \phi\rho_f)}$ and $\bar{q} = \dfrac{-\kappa i\phi^2(\nabla p - \omega^2\rho_f\bar{u})}{i\phi^2 + \kappa\omega(\rho_a + \phi\rho_f)}$ In these equations, u is displacement, p is pore-pressure, $\mu$ is shear modulus, $\lambda$ is compressional modulus, $\phi$ is porosity, $\kappa$ is the hydraulic conductivity, $\omega$ is the vibration frequency, $\rho_f$ is the fluid density, and $\rho_a$ is the apparent mass density. While $\beta$ is simply a compilation of material parameters, q represents the fluid flux and is shown in an expanded Darcy's Law form. The model then builds a stiffness matrix [A($\theta$)] and a forcing vector {b} using boundary conditions determined appropriate for the environment in which the material resides. The model then calculates an unknown solution vector $\{U_C\}$ as $\{U_C\}=[A(\theta)]^{-1}\{b\}$ where [A] is given as $$[A] = \begin{bmatrix} a_{11} & a_{12} & a_{13} & a_{14} \\ a_{21} & a_{22} & a_{23} & a_{24} \\ a_{31} & a_{32} & a_{33} & a_{34} \\ a_{41} & a_{42} & a_{43} & a_{44} \end{bmatrix}$$

with $$a_{11} = \left\langle (2\mu+\lambda)\frac{\partial\phi_j}{\partial x}\frac{\partial\phi_i}{\partial x} + \mu\left(\frac{\partial\phi_j}{\partial y}\frac{\partial\phi_i}{\partial y} + \frac{\partial\phi_j}{\partial z}\frac{\partial\phi_i}{\partial z}\right) - \omega^2(\rho - \beta\rho_f)\phi_j\phi_i \right\rangle$$

$$a_{12} = \left\langle \lambda\frac{\partial\phi_j}{\partial y}\frac{\partial\phi_i}{\partial x} + \mu\frac{\partial\phi_j}{\partial x}\frac{\partial\phi_i}{\partial y} \right\rangle$$

$$a_{13} = \left\langle \lambda\frac{\partial\phi_j}{\partial z}\frac{\partial\phi_i}{\partial x} + \mu\frac{\partial\phi_j}{\partial x}\frac{\partial\phi_i}{\partial z} \right\rangle$$

$$a_{14} = \left\langle (1-\beta)\frac{\partial\phi_j}{\partial x}\phi_i \right\rangle$$

$$a_{21} = \left\langle \lambda\frac{\partial\phi_j}{\partial x}\frac{\partial\phi_i}{\partial y} + \mu\frac{\partial\phi_j}{\partial y}\frac{\partial\phi_i}{\partial x} \right\rangle$$

$$a_{22} = \left\langle (2\mu+\lambda)\frac{\partial\phi_j}{\partial y}\frac{\partial\phi_i}{\partial y} + \mu\left(\frac{\partial\phi_j}{\partial x}\frac{\partial\phi_i}{\partial x} + \frac{\partial\phi_j}{\partial z}\frac{\partial\phi_i}{\partial z}\right) - \omega^2(\rho - \beta\rho_f)\phi_j\phi_i \right\rangle$$

$$a_{23} = \left\langle \lambda\frac{\partial\phi_j}{\partial z}\frac{\partial\phi_i}{\partial y} + \mu\frac{\partial\phi_j}{\partial y}\frac{\partial\phi_i}{\partial z} \right\rangle$$

$$a_{24} = \left\langle (1-\beta)\frac{\partial\phi_j}{\partial y}\phi_i \right\rangle$$

$$a_{31} = \left\langle \lambda\frac{\partial\phi_j}{\partial x}\frac{\partial\phi_i}{\partial z} + \mu\frac{\partial\phi_j}{\partial z}\frac{\partial\phi_i}{\partial x} \right\rangle$$

$$a_{32} = \left\langle \lambda\frac{\partial\phi_j}{\partial y}\frac{\partial\phi_i}{\partial z} + \mu\frac{\partial\phi_j}{\partial z}\frac{\partial\phi_i}{\partial y} \right\rangle$$

$$a_{33} = \left\langle (2\mu+\lambda)\frac{\partial\phi_j}{\partial z}\frac{\partial\phi_i}{\partial z} + \mu\left(\frac{\partial\phi_j}{\partial x}\frac{\partial\phi_i}{\partial x} + \frac{\partial\phi_j}{\partial y}\frac{\partial\phi_i}{\partial y}\right) - \omega^2(\rho - \beta\rho_f)\phi_j\phi_i \right\rangle$$

$$a_{34} = \left\langle (1-\beta)\frac{\partial\phi_j}{\partial z}\phi_i \right\rangle$$

$$a_{34} = \left\langle (1-\beta)\frac{\partial\phi_j}{\partial z}\phi_i \right\rangle$$

$$a_{41} = \left\langle i\omega\left(\frac{\partial\phi_j}{\partial x}\phi_i + \beta\phi_j\frac{\partial\phi_i}{\partial x}\right) \right\rangle$$

$$a_{42} = \left\langle i\omega\left(\frac{\partial\phi_j}{\partial y}\phi_i + \beta\phi_j\frac{\partial\phi_i}{\partial y}\right) \right\rangle$$

$$a_{43} = \left\langle i\omega\left(\frac{\partial\phi_j}{\partial z}\phi_i + \beta\phi_j\frac{\partial\phi_i}{\partial z}\right) \right\rangle$$

$$a_{44} = \left\langle -\frac{\beta i}{\rho_f\omega}\left(\frac{\partial\phi_j}{\partial x}\frac{\partial\phi_i}{\partial x} + \frac{\partial\phi_j}{\partial y}\frac{\partial\phi_i}{\partial y} + \frac{\partial\phi_j}{\partial z}\frac{\partial\phi_i}{\partial z}\right) \right\rangle$$

and $$\{U_C\} = \begin{Bmatrix} \hat{u} \\ \hat{v} \\ \hat{w} \\ \hat{p} \end{Bmatrix}$$

$$\{b\} = \begin{Bmatrix} \hat{x} \cdot \left[\oint (\hat{n}\cdot\sigma_E)\phi_i ds\right] \\ \hat{y} \cdot \left[\oint (\hat{n}\cdot\sigma_E)\phi_i ds\right] \\ \hat{z} \cdot \left[\oint (\hat{n}\cdot\sigma_E)\phi_i ds\right] \\ \left[\oint (\hat{n}\cdot\nabla_q)\phi_i ds\right] \end{Bmatrix}$$

The solution, displacement field $U_C$, is then used with the full stiffness matrix [A] to estimate the force. A forward solve is performed to calculate the normal stresses (seen in {b}). Since force is given simply as $$F = \frac{\sigma}{A},$$

a summation of the perpendicular stresses ($\hat{z}$) along the top surface and the cross-sectional area of the material allow for an estimation of the total normal force on the material. This force is compared to the DMA-acquired force to see how close the estimated material properties are to real properties, where the error ($\Phi$) is given as $$\Phi(\theta) = \sum_{j=1}^{D} \left( \sum_{i=1}^{N} (F_{i,j}^c(\theta) - F_{i,j}^m(\theta))(F_{i,j}^c(\theta) - F_{i,j}^m(\theta))^* \right)$$

where $\theta$ is the material property, $F^c_{i,j}$ is the calculated force and $F^m_{i,j}$ is the measured force, $*$ represents the complex conjugate, N represents the number of nodes, and D represents the number of actuation axes.

The poroelastic model is used as a forward calculation in the parameter convergence routine 137. Pseudocode of the convergence routine is as follows:

```
    DO Forward Calculation, [A(θ)]{U_C} = {b}, to calculate F_C, the total force
on the top surface
    BUILD Stiffness Matrix [A(θ)]
    BUILD forcing vector {b}
    CALCULATE U_C = [A(θ)]^-1 {b}
    CALCULATE {b} = [A(θ)]{U_C}
    FOR 1 to Number of Nodes
        IF Node is on top surface
            F_C = F_C + b(node)
        ENDIF
    ENDFOR
ENDDO
CALCULATE Squared Error between Measured and Calculated Force Values
    SQUARED_ERROR = ||F_C - F_M||
DOWHILE (SQUARED_ERROR < TOLERANCE or ITERATION > MAXIMUM)
  ➤ CALCULATE MATERIAL PROPERTY UPDATE
    IF ITERATION = 1, Perform Steepest Gradient Descent
```
$$\text{CALCULATE property gradient for } \theta \rightarrow \frac{\partial \Phi}{\partial \theta} = \frac{\Phi(\theta + \Delta\theta) - \Phi(\theta - \Delta\theta)}{2\Delta\theta}$$
```
    CALCULATE property update using Armijo Linesearch Algorithm
    ADD update to θ_1 and θ_2
    ELSEIF ITERATION > 1, Perform Gauss-Newton Method
```
$$\text{CALCULATE property gradient (g) for } \theta \rightarrow \frac{\partial \Phi}{\partial \theta} = \frac{\Phi(\theta + \Delta\theta) - \Phi(\theta - \Delta\theta)}{2\Delta\theta}$$
```
    CALCULATE property Hessian (H) for θ →
```
$$\frac{\partial^2 \Phi}{\partial \theta_1 \partial \theta_2} = \frac{\Phi(\theta_1 + \Delta\theta_1, \theta_2 + \Delta\theta_2) - \Phi(\theta_1 - \Delta\theta_1, \theta_2 + \Delta\theta_2) \ldots}{4\Delta\theta_1 \Delta\theta_2}$$
$$\frac{-\Phi(\theta_1 + \Delta\theta_1, \theta_2 - \Delta\theta_2) + \Phi(\theta_1 - \Delta\theta_1, \theta_2 - \Delta\theta_2)}{4\Delta\theta_1 \Delta\theta_2}$$
```
    APPLY Joachimowicz and Levenberg-Marquadt regularization
    CALCULATE property update p = H^-1 g
    ADD update to θ_1 and θ_2
    ENDIF
    RECALCULATE Forward solution U_C
    RECALCULATE Calculated Force F_C
    CALCULATE Squared Error between Measured and Calculated Force Values
    ITERATION = ITERATION + 1
ENDDOWHILE
```

Once the poroelastic model parameters (shear modulus, hydraulic conductivity, and Poisson's ratio) for the sample are determined, a second mechanical model of in-vivo tissue, such as a computerized mechanical model of brain, based upon the poroelastic equations, is constructed. In a particular embodiment, the second mechanical model is then executed, with displacements observed during surgery, to model displacement of a tumor within the tissue during neurosurgery caused by the displacements.

While the term "load cell" has been used to describe a force-measuring device in describing the DMA, it is anticipated that other force-measuring devices, including those that rely on piezoelectric responses or measuring displacement of a spring or elastomeric substance to which force is applied.

In an embodiment, the DMA obtains measurements, and fits the parameters of poroelastic model to the measurements at several discrete frequencies in the range from 1 to 30 Hz. In a particular embodiment, frequencies of 2, 4, 6, 8, 10, 12, and 14 Hz. are used.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A system for determining poroelastic mechanical properties of porous materials comprising: a dynamic mechanical analyzer comprising an actuator and a force measuring device, the actuator adapted to apply a displacement in a first axis to the porous materials over a range of frequencies, and the force measuring device is adapted to measure a mechanical response of the porous materials, wherein the actuator is configured to apply the displacement to the porous materials through a first nonslip surface, the system configured to hold the porous materials on a second nonslip surface; at least one processor coupled to drive the actuator to apply the displacement to the porous materials and to read the mechanical response of the porous materials, the at least one processor also being configured to execute machine-readable instructions of a poroelastic material model recorded in a memory;

the memory also containing limits;

the memory further containing machine-readable instructions which are implemented on the at least one processor, to cause the at least one processor to perform a convergence procedure configured to determine parameters for the poroelastic material model such that the porous material model, when executed using the determined parameters to simulate a mechanical response, produces an estimated porous materials response that matches the measured mechanical response of the porous materials to within the limits.

2. The system of claim 1 further comprising a magnetic resonance elastography (MRE) system, and wherein the determined parameters are used to validate material property values acquired by the MRE system.

3. The system of claim 1 wherein the dynamic mechanical analyzer is configured to measure the response of the porous material over a plurality of frequencies, and wherein the machine-readable instructions of the convergence procedure use the response over that plurality of frequencies to determine the model parameters.

4. The system of claim 1 wherein the determined parameters are provided to a computer model of displacement of tumor tissue during neurosurgery.

5. A system for modeling mechanical responses of tissue, comprising the system of claim 4, the processor configured to execute a second mechanical model of in-vivo tissue incorporating a modeled location of a tumor, the processor configured to execute the second mechanical model, and the second mechanical model is configured with the determined parameters.

6. The system of claim 1 wherein the poroelastic model is derived from Biot's theory of consolidation implementing the equations:

$$\nabla \cdot \mu(\nabla \bar{u} + \nabla \bar{u}^T) + \nabla(\lambda \nabla \cdot \bar{u}) - (1-\beta)\nabla \bar{p} = -\omega^2(\rho - \beta\rho_f)\bar{u}$$
$$i\omega(\nabla \cdot \bar{u}) - \nabla \cdot \bar{q} = 0$$

where $\beta = \dfrac{\omega\phi^2 \rho_f \kappa}{i\phi^2 + k\omega(\rho_a + \phi\rho_f)}$ and $\bar{q} = \dfrac{-\kappa i\phi^2(\nabla p - \omega^2 \rho_f \bar{u})}{i\phi^2 + \kappa\omega(\rho_a + \phi\rho_f)}$ and where, u is displacement, p is pore-pressure, μ is shear modulus, λ is compressional modulus, φ is porosity, κ is a hydraulic conductivity, ω is a vibration frequency, $\rho_f$ is a fluid density, and $\rho_a$ is an apparent mass density, β is a compilation of material parameters, and q represents a fluid flux within the porous material.

7. The system of claim 3 wherein the plurality of frequencies lie within a range from one to thirty hertz.

8. The system of claim 1 further comprising a second actuator coupled to provide a displacement to the material in a second axis perpendicular to the first axis.

9. The method of claim 5 wherein the tissue is brain tissue.

10. The system of claim 4, wherein the tissue is brain tissue, wherein the poroelastic material model is configured with a pre-surgical location of a tumor derived from pre-surgical medical imaging; and further comprising apparatus configured to observe a displacement of the material; and executing the mechanical model with the observed displacement to determine tumor shift during surgery.

11. The system of claim 1, wherein the poroelastic material model incorporates a non-slip boundary condition to better estimate hydraulic conductivity.

12. A method for determining parameters of a computerized poroelastic model of a material comprising:

using a processor coupled to drive an actuator, applying a displacement through a non-slip surface to a sample of the material, the sample coupled to a second non-slip surface, at a particular frequency selected from a plurality of frequencies;

measuring, with a force measuring device, a mechanical response of the material to the applied displacement;

executing, on the processor, machine readable instructions of the poroelastic computer model of mechanical properties of the material, the machine readable instructions being recorded in a memory, the memory also containing limits; and converging parameters for the poroelastic model such that the model, when simulating the applied displacement, produces an estimated porous materials response of the tissue that matches the measured mechanical response to within the limits.

13. The method of claim 12, wherein the material is brain tissue, and further comprising:

configuring the computerized poroelastic model with a pre-surgical location of a tumor derived from pre-surgical medical imaging;

observing a displacement of the porous material; and executing the computerized poroelastic model with the observed displacement to determine tumor shift during surgery.

* * * * *